United States Patent [19]

Bruce

[11] Patent Number: 4,478,080
[45] Date of Patent: Oct. 23, 1984

[54] DEWPOINT MEASUREMENT SYSTEM FOR NEAR SATURATION CONDITIONS

[75] Inventor: Charles W. Bruce, Las Cruces, N. Mex.

[73] Assignee: The United States of America as represented by the Secretary of the Army, Washington, D.C.

[21] Appl. No.: 508,688

[22] Filed: Jun. 28, 1983

[51] Int. Cl.³ .............................................. G01N 25/66
[52] U.S. Cl. ......................................... 73/335; 374/28
[58] Field of Search ....................... 73/335, 336, 336.5, 73/338, 338.3, 338.6, 29; 374/28

[56] References Cited
U.S. PATENT DOCUMENTS
2,633,024  3/1953  Lamb .................................. 73/338.6

Primary Examiner—Gerald Goldberg
Assistant Examiner—Joseph W. Roskos
Attorney, Agent, or Firm—Anthony T. Lane; Robert P. Gibson; Saul Elbaum

[57] ABSTRACT

A dewpoint sensor has an inlet connected to a gas flow switch that first admits air at 100 percent saturation at ambient temperature for determining a reference dewpoint temperature. The switch then connects the sensor to ambient air for determining the ambient dewpoint temperature. Entry of this temperature data in standard tables establishes relative humidity with improved accuracy at high humidity due to the measurement of both temperatures on the same sensor instrument.

10 Claims, 2 Drawing Figures

DEWPOINT MEASUREMENT SYSTEM FOR NEAR SATURATION CONDITIONS

RIGHTS OF THE GOVERNMENT

The invention described herein may be manufactured, used, and licensed by or for the U.S. Government for governmental purposes without the payment to me of any royalty thereon.

FIELD OF THE INVENTION

The present invention relates to humidity measuring apparatus and more particularly to a photo-optical system for obtaining accurate measurements near saturation.

BRIEF DESCRIPTION OF THE PRIOR ART

The prior art includes a wide variety of instruments for photo-optically determining dewpoint temperature. A well-accepted commercially available condensation plate dewpoint hygrometer which has widespread use for measuring dewpoint is the EG & G Model 880 system. This particular system includes a sensor portion, which operates as an absolute device, consisting of a Kelvin cooler-heater with an optical quality surface for detection of dewpoint temperature. In operating this type of device, the normal procedure to follow involves independent measurements of ambient and dewpoint temperatures together with their absolute errors. The error factor increases as saturation of the air is approached.

Accordingly, there is need for an improvement of existing apparatus which will remove various measurement uncertainties, particularly affecting the accuracy of the instrumentation at high relative humidity.

BRIEF DESCRIPTION OF THE PRESENT INVENTION

The present invention is capable of accurate relative humidity measurements near saturation because the instrumentation obtains a reference dewpoint temperature by sampling air from a saturated plenum at ambient temperature. A reservoir of liquid water in the plenum maintains saturation. This plenum, in series with the dewpoint sensor, such as included in the previously mentioned EG & G instrument form a closed circulation circuit. A saturation dewpoint temperature is determined during this reference phase of instrumentation use. The system is then switched to ambient atmosphere for a measurement of the ambient dewpoint temperature. These determined temperatures are parameters for well-established charts from which relative humidity may be determined. An accurate reading of the relative humidity is obtained because measurements for saturation and ambient dewpoint temperatures are obtained on the same instrument as opposed to being obtained independently, as was the case with the prior art.

The above-mentioned objects and advantages of the present invention will be more clearly understood when considered in conjunction with the accompanying drawings, in which:

DETAILED DESCRIPTION OF THE INVENTION

Figure 1:
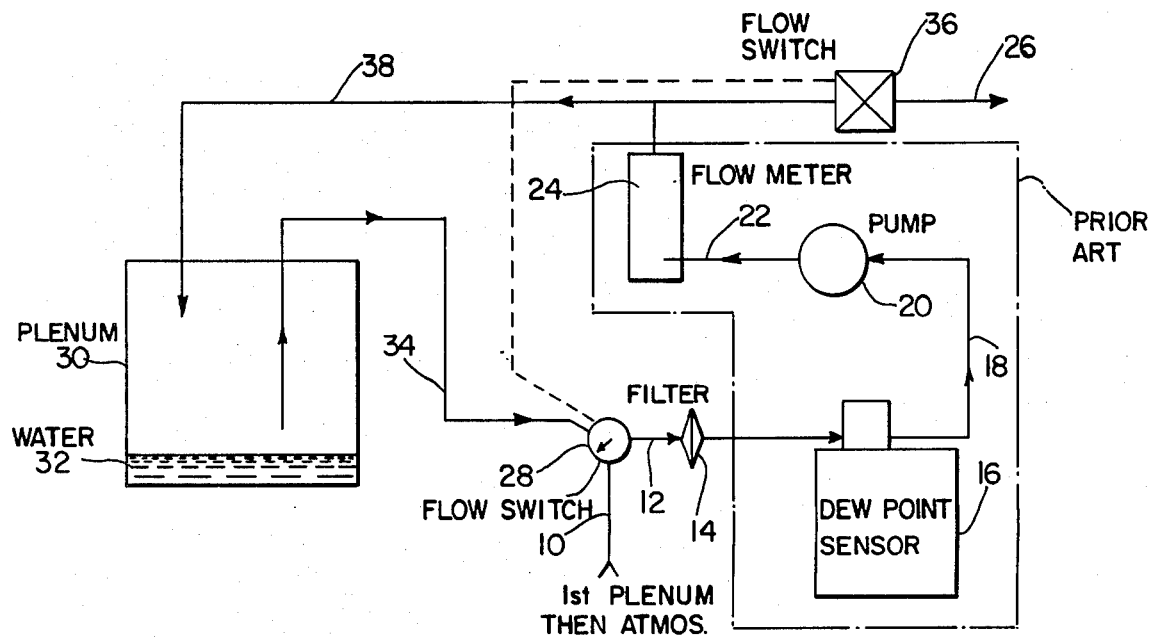
FIG. 1 is a block diagram of the present system.

Referring to FIG. 1, the present system is seen to include an inlet 10 open to the ambient atmosphere. Air passes through pipe 12. Particulate matter is filtered at 14 and then introduced to a prior art instrument, such as the EG & G instrument previously mentioned. The filter is preferably a submicron filter which will greatly reduce particulate contamination of the Kelvin optical plate located within the prior art instrument dewpoint sensor 16. Upon measurement of the dewpoint temperature by sensor 16, the air is transported through pipe 18 in response to pressure from a serially connected pump 20, the outlet pipe 22 of which is connected to flow meter 24 which regulates the airflow through the sensor 16. The sensor 16 is preferably an absolute device including a Kelvin cooler-heater with an optical quality surface for detection of dewpoint temperature. The prior art instrument indicated in FIG. 1 is a microprocessor based photo-optical instrument which determines dewpoint temperature automatically.

In conventional utilization of the prior art instrument, the outlet of flow meter 24 is simply ported to the atmosphere as indicated at 26. However, in order to obtain the objectives of the present invention, an internal reference dewpoint temperature must be established. Toward this end, a two position flow switch 28 has one inlet connected to the ambient inlet 10 while a second switch inlet is connected to the outlet pipe 34 of a plenum 30 which is partially filled with water 32 for sufficient time to completely saturate the air within the plenum 30. The outlet of switch 28 is permanently connected to pipe 12.

Flow switch 28 is connected to flow switch 36 so that the circulation pattern for the invention may be changed to cause measurement of air from plenum 30 which is 100 percent saturated at ambient temperature. This occurs when switch 28 has its position changed whereby plenum outlet pipe 34 is connected to pipe 12 and flow switch 36 is switched to a second position whereby air flowing from flow meter 24 is circulated through inlet pipe 38 of plenum 30. With flow switches 28 and 36 set as just described, a recirculation of 100 percent saturated air at ambient will occur between plenum 30 and the dewpoint sensor 16.

In operation of the device illustrated in FIG. 1, switch 28 is first set to direct 100 percent saturated air at ambient temperature from plenum 30 to dewpoint sensor 16. A measurement of the dewpoint temperature is then made and will serve as a first parameter for entry into standard charts for deriving relative humidity. The second aspect of operation is the switching of flow switch 28 to a second position whereby ambient atmosphere flows through inlet 10 to the dewpoint sensor 16 for measurement of ambient dewpoint temperature. After this has been achieved, the second parameter for entry in the relative humidity charts is obtained so that the relative humidity may be determined. In the event the relative humidity is quite high in the ambient atmosphere, the present invention will permit a far more accurate reading of the relative humidity than is achieveable by the prior art instrument alone.

Figure 2:
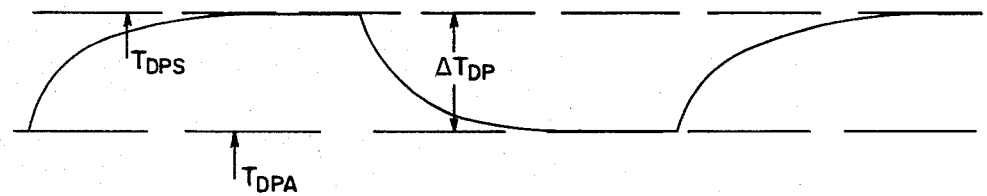
FIG. 2 is a plot of temperature obtained during sample cycling by the present invention.

In FIG. 2, a plot is shown of the cyclical process for measurement of relative humidity. The upper level of the curve indicated by $T_{DPS}$ corresponds with the dewpoint temperature of the saturated air from the plenum. The lower temperature level indicated as $T_{DPA}$ indicates the dewpoint temperature of the ambient atmosphere. The achievement of the present invention becomes manifest when errors in absolute values of the two temperatures are much less important, i.e., the different in $\Delta T_{DP} = T_{DPS} - T_{DPA}$ is small at high relative humidity. Thus, the relative humidity by the internal reference method described is much more direct and accurate than by using the conventional procedure involving independent measurement of the ambient and dewpoint temperatures together with their absolute errors.

It should be understood that the invention is not limited to the exact details of construction shown and described herein for obvious modifications will occur to persons skilled in the art.

I claim:

1. A system for measuring dewpoint temperature comprising:
   means for measuring the dewpoint temperature of air delivered to an inlet thereof;
   plenum means for containing water therein and saturating the air contained therein while at ambient temperature;
   first flow switching means connected in a first position thereof between the plenum means and the measuring means for directing the saturated air to the measuring means for determining the dewpoint thereof; and
   ambient air inlet means connected to a second position of the flow switching means for selectively directing ambient air to the measuring means for determining the dewpoint thereof;
   wherein determination of the dewpoint temperatures of the ambient and saturated air are determinative of the relative humidity of the ambient air.

2. The apparatus set forth in claim 1 together with second flow switching means connected to the first flow switching means and actuatable therewith for venting ambient air after its passage through the measuring means, the second flow switching means being switched to recirculate the saturated air to the plenum means after its passage through the measuring means.

3. The apparatus of claim 1 together with a pump connected to the measuring means for drawing air through the measuring means.

4. The apparatus set forth in claim 1 together with flow metering means connected to the measuring means for regulating the flow of air through the measuring means.

5. The apparatus set forth in claim 2 together with a pump connected to the measuring means for drawing air through the measuring means.

6. The apparatus set forth in claim 5 together with flow metering means connected to the measuring means for regulating the flow of air through the measuring means.

7. The apparatus set forth in claim 6 together with means serially connected to the inlet of the measuring means for filtering out particulate contamination.

8. The method for accurately determining high levels of relative humidity, the steps comprising:
   subjecting a measurment apparatus to saturated air at ambient temperature for determining the dewpoint temperature thereof;
   subsequently switching the same apparatus to ambient air for determining the dewpoint temperature thereof; and
   entering relative humidity charts with the dewpoint temperatures for determining the relative humidity of the ambient air.

9. A method for accurately determining high levels of relative humidity, the steps comprising:
   providing saturated air at ambient temperature to a dewpoint temperature measuring device through a flow switch in a first position for determining the dewpoint temperature of the saturated air;
   recirculating the saturated air through the device during the temperature determination;
   providing ambient air to the same device, after switching the flow switch to a second position for determining the dewpoint temperature of the ambient air;
   ceasing the recirculation during dewpoint temperature determination of the ambient air;
   venting the ambient air to the atmosphere after the device has determined the ambient air dewpoint temperature;
   entering relative humidity charts with the dewpoint temperatures for determining the relative humidity of the ambient air.

10. The method set forth in claim 9 together with the step of filtering air provided to the device for eliminating particulate contamination.

* * * * *